US00PP36807P2

(12) United States Plant Patent
Wood

(10) Patent No.: US PP36,807 P2
(45) Date of Patent: Jul. 8, 2025

(54) ***RIBES* PLANT NAMED 'SMROCS'**

(50) Latin Name: *Ribes odoratum*
Varietal Denomination: SMROCS

(71) Applicant: Spring Meadow Nursery, Grand Havem, MI (US)

(72) Inventor: Timothy D. Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 18/966,355

(22) Filed: Dec. 3, 2024

(51) Int. Cl.
*A01H 5/00* (2018.01)
*A01H 6/00* (2018.01)

(52) U.S. Cl.
USPC ..... Plt./156

(58) Field of Classification Search
USPC ..... Plt./156, 226
See application file for complete search history.

(56) References Cited

PUBLICATIONS https://raintreenursery.com/products/missouri-giant-currant?; Retrieved from the Internet on Mar. 4, 2025.*

* cited by examiner

*Primary Examiner* — Susan McCormick Ewoldt
(74) *Attorney, Agent, or Firm* — Cassandra Bright

(57) ABSTRACT

A new and distinct cultivar of *Ribes* plant named 'SMROCS' is disclosed, characterized by highly floriferous plants producing abundant bright yellow flowers beginning in mid-Spring. Plants have a compact, well-branched habit. Flowers have a pleasant clove scent. Abundant edible black fruits are produced. Plants have shown a high tolerance for drought conditions. The new variety is a *Ribes*, normally produced as an outdoor garden plant.

2 Drawing Sheets

Latin name of the genus and species: *Ribes odoratum.*
Variety denomination: 'SMROCS'.

BACKGROUND OF THE INVENTION

The new *Ribes* cultivar is a product of open pollination conducted by the inventor, Timothy Wood, in Grand Haven, Michigan. The objective of the breeding program was to produce new *Ribes* colors and habits. The open-pollination resulting in this new variety was made during the Summer 2011.

The seed parent is the variety *Ribes odoratum* 'Crandall', unpatented. The new variety was identified as a potentially interesting selection in Summer 2016, at a commercial nursery in Grand Haven, Michigan.

Asexual reproduction of the new cultivar 'SMROCS' by softwood cuttings was first performed in 2016, at a nursery in Grand Haven, Michigan. Subsequent propagation has shown that the unique features of this cultivar are stable and reproduced true to type in multiple successive generations.

SUMMARY OF THE INVENTION

The cultivar 'SMROCS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMROCS' These characteristics in combination distinguish 'SMROCS' as a new and distinct *Ribes* cultivar;

1. Highly floriferous plants produce abundant bright yellow flowers beginning in mid-Spring.
2. Compact, well-branched plant habit.
3. Flowers have a pleasant clove scent.
4. Abundant edible black fruits are produced.
5. High tolerance for drought conditions.

PARENT COMPARISON

Plants of the new cultivar 'SMROCS' are similar to plants of the seed parent in most horticultural characteristics, however, plants of the new cultivar 'SMROCS' differ in the following;

1. Plants of the new cultivar are compact whereas the seed parent is leggy and rangy.
2. The new cultivar is well-branched; the seed parent is loosely branched.

COMMERCIAL COMPARISON

Plants of the new cultivar 'SMROCS' can be compared to the commercial species *Ribes aureum* var. *aureum*, unpatented. These plants are similar in most horticultural characteristics, however 'SMROCS' differs in the following;

1. The new cultivar has a compact plant habit, whereas this comparator has a very loose, spreading habit.

BRIEF DESCRIPTION OF THE PHOTOGRAPHS

Figure 1:
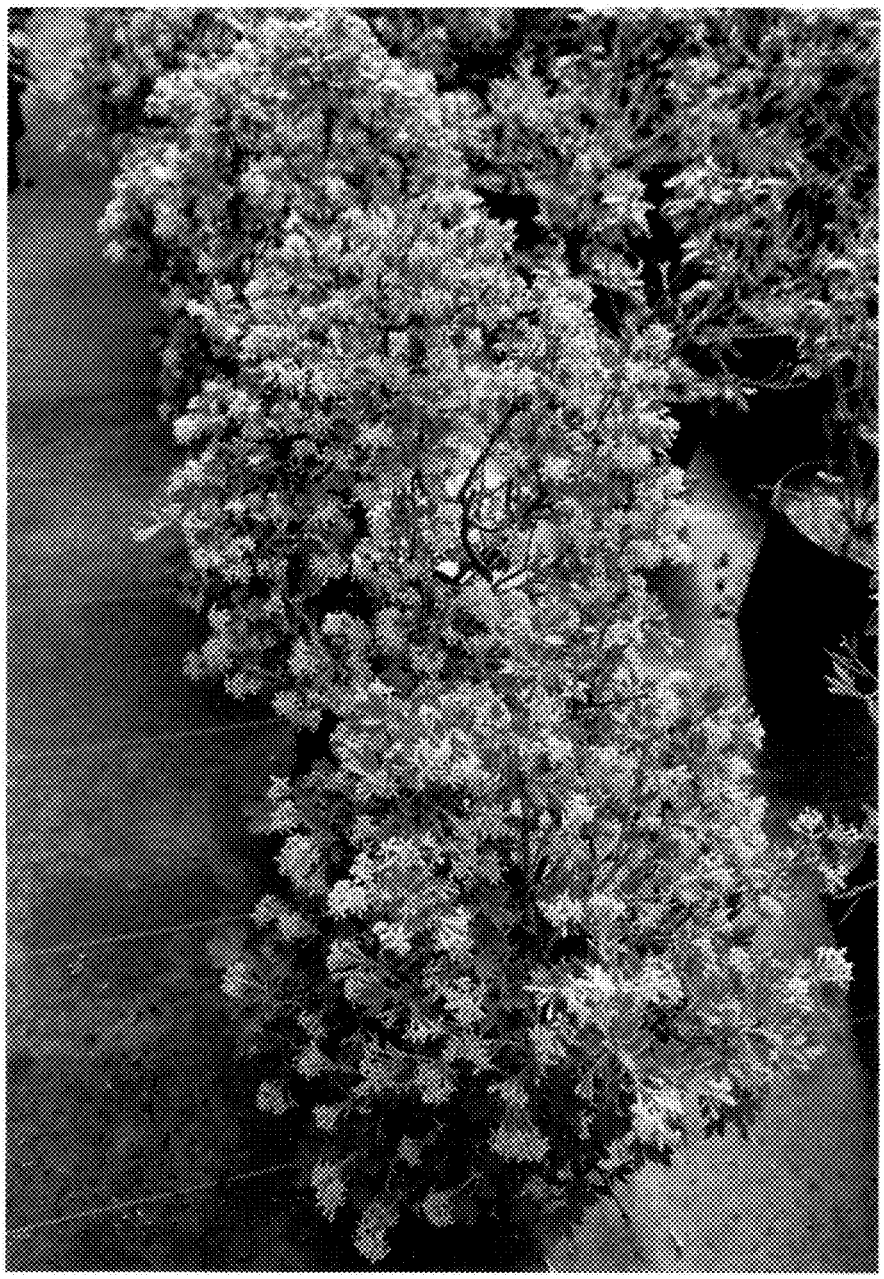

The accompanying photograph in FIG. 1 illustrates in full color typical plants of 'SMROCS' in full bloom grown outdoors in 3-gallon pots at about 2 years of age.

Figure 2:
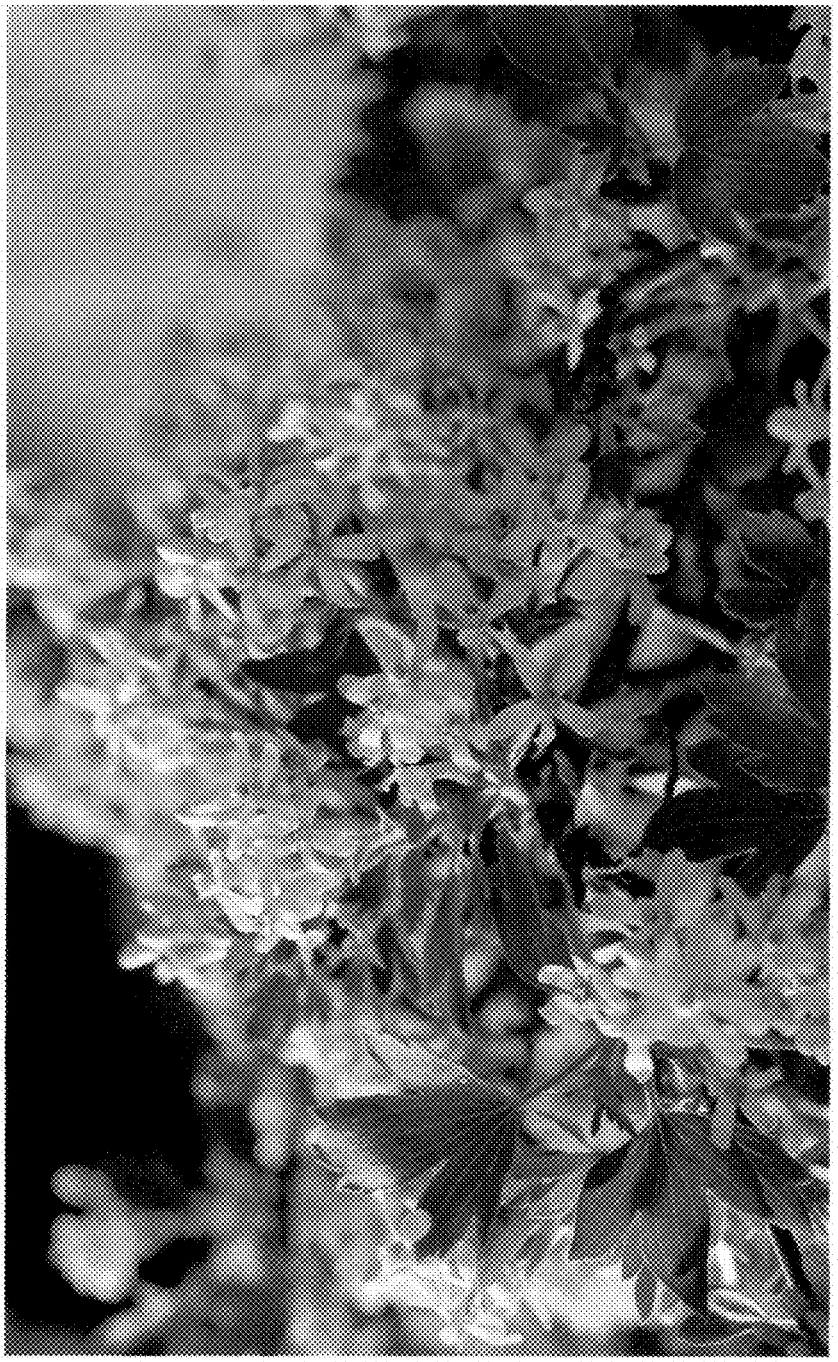

FIG. 2 illustrates typical flowers of the new cultivar.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMROCS' plants grown in a polyhouse in Grand Haven, MI. Measurements were taken during Spring of 2021. The plants were 2 to 3 years old. The growing temperature ranged from approximately 5° C. to 27° C. Measurements and numerical values represent averages of typical plant types.

Botanical classification: *Ribes odoratum* 'SMROCS'.

PROPAGATION

Time to initiate roots: Approximately 10 to 14 days.

Root description: Density is dense and freely branching. Thin and fibrous. Tan/yellow in color, not effectively measured with a color chart.

Time to produce a rooted young plant: Approximately 60 days.

PLANT

Plant type: Perennial shrub.

Age of plant described: Approximately 2 years old.

Growth habit: Upright and slightly outward.

Pot size of plant described: 3 gallon container.

Overall plant shape: Compact and round.

Height: 65 cm.

Plant spread: 50 cm.

Growth rate: Rapid.

Plant vigor: HIGH.

Branching characteristics: Basal, free branching, encouraged by some pinching.

Length of primary lateral branches: 40 cm.

Diameter of lateral branches: 5 mm.

Quantity of lateral branches: About 20.

Stem:

- *Stem characteristics*.—Rounded.
- *Stem strength*.—Strong.
- *Aspect*.—Straight, growing at about 45° from center.
- *Color*.—New Growth: Yellow-Green 145B. Old Growth: Brown 200D.
- *Texture*.—New growth slightly pubescent. Old growth glabrous.

Internode length: Average 1.5 to 3 cm.

FOLIAGE

Leaf:

- *Arrangement*.—Alternate or sub alternate, rotating around stem.
- *Leaf shape*.—Palmate.
- *Average length*.—Approximately 4.5 cm.
- *Average width*.—5 cm.
- *Apex*.—Acute.
- *Base*.—Truncate.
- *Margin*.—Serrate.
- *Texture of top surface*.—Soft and velvety pubescence.
- *Texture of bottom surface*.—Soft and velvety pubescence.
- *Color*.—Young foliage upper side: Near RHS Yellow-Green 146B. Young foliage under side: Near RHS Yellow-Green 146B. Mature foliage upper side: RHS Green 137B. Mature foliage under side: RHS Yellow-Green 147B. Venation: Pattern: Pinnate. Color upper side: RHS Yellow-Green 146D. Color under side: RHS Yellow-Green 146D.
- *Petiole*.—Length: 3 cm. Diameter: 1.5 mm. Petiole color upper side: RHS Yellow-Green 146D. Petiole color lower side: RHS Yellow-Green 146D. Petiole Texture: Soft pubescence.
- *Other foliage characteristics*.—Excellent durability to environmental stressors.

FLOWER

Natural flowering season: April to May in Michigan.

Quantity of flowers and buds per plant: 3000 to 4000.

Individual flowers:

- *Flower shape*.—Salverform.
- *Flower aspect*.—Mostly outward, some upward.
- *Flowering arrangement*.—Single salverform flowers terminally clustered in groups of 4 to 5.
- *Size*.—Diameter: 1 cm. Depth: 1.5 cm. Throat diameter: 2 mm. Flower tube length: 1.25 cm Flower tube diameter, base: 2 mm.
- *Persistence*.—Persistent.
- *Fragrance*.—Clove scent.

Bud:

- *Shape*.—Obovate to spatulate.
- *Length*.—1 cm.
- *Diameter*.—2 mm.
- *Color*.—RHS Yellow 8A.

Petal:

- *Petal arrangement*.—Whorled, fused at opening of throat.
- *Number of petals per flower*.—6.
- *Petal shape*.—Oblong.
- *Petal base*.—Fused at throat.
- *Margin*.—Entire.
- Tip shape.—Obtuse.
- *Length*.—7 mm from throat.
- *Width*.—3 mm.
- *Texture*.—Upper: Soft, silky. Lower: Soft, silky.
- *Color*.—When opening: Upper side: RHS Yellow 8A. Under side: RHS Yellow 8A. Fully open: Upper side: RHS Yellow 8A. Under side: RHS Yellow 8A.
- *Flower tube*.—Color: RHS Yellow 8A, interior and exterior.
- *Throat*.—Texture: Soft, smooth. Color: RHS Yellow 8A.

Petaloids:

- *Quantity*.—6.
- *Arrangement*.—Whorled petaloids fused at opening of throat.
- *Size*.—3 mm in length, 1 mm in length.
- *Shape*.—Oblong.
- *Margin*.—Entire.
- *Texture*.—Smooth and silky.
- *Color*.—Yellow 8A.

Sepal: No sepals present, flower tube fuses directly with ovary at base.

Peduncle:
*Length.*—5 mm.
*Diameter.*—1 mm.
*Color.*—RHS Yellow-Green N144C.
*Orientation.*—15-30° from branch.
*Strength.*—Slightly pubescent.
*Texture.*—Smooth.
Pedicel: None.

REPRODUCTIVE ORGANS

Stamens:
*Number.*—5.
*Filament length.*—5 mm.
*Filament color.*—RHS Yellow 8B.
Anthers:
*Shape.*—Linear, slightly oblong.
*Length.*—1 mm.
*Color.*—RHS Greyed-Green 197A.
*Pollen color.*—RHS Greyed-White 156B.
*Pollen amount.*—Low to moderate.
Pistil:
*Number.*—1.
*Length.*—1.5 cm.
*Style.*—Length: 1.5 cm. Color: RHS Yellow-Green N144B. Ovary Color: RHS Yellow-Green N144B.
Stigma:
*Color.*—RHS Green 137B.
*Shape.*—Tube-shaped, continuous with pistil.

OTHER CHARACTERISTICS

Fruit: 50 to 100 fruits per lateral branch.
*Shape.*—Round.
*Color.*—Black 203C. Glossy.
*Taste.*—Sweet and tart with a slightly spicy clove flavor.
*Seeds.*—Flattened, about 3 mm long and 2 mm wide. Chestnut brown color, near Greyed-Orange 165A flushed 166A.
Disease/pest resistance: Neither resistance nor susceptibility to normal diseases and pests of *Ribes* have been observed
Temperature tolerance: USDA Zones 4-8.
Drought tolerance: Good tolerance for drought conditions.

What is claimed is:

1. A new and distinct cultivar of *Ribes odoratum* plant named 'SMROCS' as herein illustrated and described.

* * * * *